United States Patent [19]

Pourreau et al.

[11] Patent Number: 5,371,298

[45] Date of Patent: Dec. 6, 1994

[54] PREPARATION OF DIALKYL PEROXIDES

[75] Inventors: Daniel B. Pourreau, Downingtown; Haven S. Kesling, Jr., Drexel Hill; Frank J. Liotta, Jr., Collegeville; Jeffrey M. McFarland, Brookhaven, all of Pa.

[73] Assignee: Arco Chemical Technology, L.P., Wilmington, Del.

[21] Appl. No.: 171,957

[22] Filed: Dec. 22, 1993

[51] Int. Cl.$^5$ .................................... C07C 409/16
[52] U.S. Cl. ............................ 568/578; 568/558; 568/561
[58] Field of Search ............... 568/578, 561; 562/558

[56] References Cited

U.S. PATENT DOCUMENTS

| | | | |
|---|---|---|---|
| 2,403,758 | 7/1946 | Rust et al. | 568/578 |
| 2,403,771 | 7/1946 | Vaughan et al. | 568/578 |
| 2,630,456 | 3/1953 | Bell et al. | 568/578 |
| 2,845,461 | 7/1958 | Winkler et al. | 568/570 |
| 2,862,973 | 12/1958 | Winkler et al. | 568/578 |
| 3,478,108 | 11/1969 | Grane | 568/570 |
| 3,626,014 | 12/1971 | Harvey | 568/578 |
| 4,408,081 | 10/1983 | Foster | 568/570 |

FOREIGN PATENT DOCUMENTS

| | | | |
|---|---|---|---|
| 839312 | 4/1970 | Canada | 568/578 |
| 1555308 | 12/1968 | France | 568/570 |

OTHER PUBLICATIONS

"Organic Peroxides. Part III. The Preparation of Alkyl Hydroperoxides and Dialkyl Peroxides. Characteristics Derivatives of Alkyl Hydroperoxides." Davies, et al., J. Chem. Soc., pp. 2200–2204 (1954).

Tsunoda et al "Chemical Abstracts" vol. 57 p. 2121 (1962).

*Primary Examiner*—Werren B. Lone
*Attorney, Agent, or Firm*—William C. Long

[57] ABSTRACT

The present invention provides a process the production of dialkyl peroxides by reaction of an alcohol and/or an olefin with an organic hydroperoxide, using an acidic resin catalyst, especially a highly cross-linked hydrophobic acidic resin catalyst.

7 Claims, No Drawings

PREPARATION OF DIALKYL PEROXIDES

BACKGROUND OF THE INVENTION

1. Field of the Invention

The present invention relates to the production of dialkyl peroxides such as ditertiary butyl peroxide by the reaction of an alcohol such as tertiary butyl alcohol and/or an olefin such as isobutylene with a hydroperoxide such as tertiary butyl hydroperoxide in the presence of an acidic resin catalyst.

2. Description of the Prior Art

The preparation of dialkyl peroxides by the reaction of an alcohol such as tertiary butyl alcohol (TBA) with an organic hydroperoxide such as tertiary butyl hydroperoxide (TBHP) is known. See, for example, U.S. Pat. Nos. 2,403,771, 2,403,758, 2,862,973, 3,626,014 and the like. The preparation of dialkyl peroxides by the reaction of an olefin such as 2-methylbut-2-ene with an organic hydroperoxide such as TBHP is also known. See Davies, et al., J. Chem. Sec. page 2200, 1954. Also French patent 1,555,308 shows the reaction of isobutylene with hydrogen peroxide to produce TBHP and ditertiary butyl peroxide.

In such prior processes, catalysts such as sulfuric acid, sulfonic acid resins having a low degree of cross-linking and the like have been employed. The use of such catalysts has a number of disadvantages including the corrosion and safety hazards associated with the use of sulfuric acid, catalyst deactivation and deterioration associated with the use of catalyst resins and the like. Canadian Patent 839,312, for example, shows the production of ditertiary butyl peroxide by the reaction of TBA with TBHP using a gel-type 4% cross-linked sulfonic acid resin with the requirement that water be azeotropically removed as with chloroform in order for the reaction to proceed.

The preparation of organic hydroperoxides by reaction of an alcohol such as TBA with hydrogen peroxide using an inorganic heteropoly acid is shown in U.S. Pat. No. 2,630,456.

BRIEF DESCRIPTION OF THE INVENTION

In accordance with the present invention, a process is provided for the production of dialkyl peroxides wherein an alcohol and/or an olefin is reacted with an organic hydroperoxide in the presence of an acidic resin catalyst.

When the catalyst has only a low degree of cross-linking, the hydroperoxide is reacted primarily with olefin in order to avoid the deleterious effect of water which is illustrated in Canadian Patent 839,312. In especially preferred practice where the catalyst is at least 10% cross-linked, preferably at least 20% cross-linked, the hydroperoxide can be reacted with alcohol or with olefin, or with mixtures.

DETAILED DESCRIPTION

The process of the present invention can be represented by the following equations:

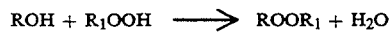

or

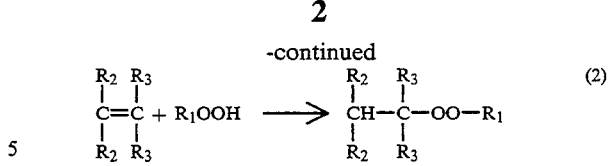

wherein R and R1 are the same or different alkyl groups having 1 to 10 carbon atoms, R2 and R3 are hydrogen or R. Preferably, R and R1 are the same tertiary alkyl group having 4 or 5 carbon atoms, i.e. tertiary butyl or tertiary amyl groups, R3 is R and R2 is hydrogen.

In especially preferred practice of the invention, ditertiary butyl peroxide is prepared by the reaction of tertiary butyl hydroperoxide with tertiary butyl alcohol and/or isobutylene, and ditertiary amyl hydroperoxide is prepared by the reaction of tertiary amyl hydroperoxide with tertiary amylene. Dialkyl peroxides where the alkyl groups are different, such as tertiary butyl tertiary amyl peroxide, can be prepared for example by reacting tertiary amyl alcohol and/or tertiary amylene with tertiary butyl hydroperoxide.

In carrying out the process of the present invention, it is generally desirable to provide at least 0.5 mols of alcohol and/or olefin per mol of hydroperoxide to the reaction. Preferably, at least 1 mol of alcohol and/or olefin per mol of hydroperoxide is employed up to about 10 mols of alcohol and/or olefin per mol of hydroperoxide. The use of alcohol and/or olefin in at least equimolar amounts relative to the hydroperoxide provides good reaction rates and high conversions of the reactants.

Where a highly cross-linked acidic resin catalyst is employed, the reaction of the invention can be carried out using either alcohol or olefin to react with the hydroperoxide. Preferably, however, mixtures of 0.1 to 10 mols of alcohol per mol of olefin are employed.

Where the catalyst does not have a high degree of cross-linking, the reaction of the invention is carried out using olefin as a primary reactant with the hydroperoxide. Mixtures containing up to about 1.0 mols of alcohol per mol of olefin are employed.

The process of the invention is carried out at temperatures sufficiently high to ensure a satisfactory reaction rate but not so high as to cause substantial decomposition of the hydroperoxide. Generally, temperatures ranging from about 20° C. to 150° C. and preferably 40° C. to about 110° C. are employed. The reaction takes place in the liquid phase, and the system pressure is maintained at a level sufficient to ensure the liquid phase reaction. Pressures in the range 0.2 to 100 atmospheres gauge are illustrative.

Essential to preferred practice of the invention is the use of an acidic ion exchange resin which is highly cross-linked, is at least 10% cross-linked, and thus oxidation resistant and hydrophobic as catalyst. As a result of the use of such catalysts, water removal requirements, previously required, are not necessary in carrying out the process and alcohol can be used to react with the hydroperoxide.

Resins which are employed in carrying out the invention are preferably polystyrene-divinyl benzene resins which are at least 10% cross-linked. As used herein, the degree of cross-linking refers to the use of sufficient cross-linking agent, e.g. divinyl benzene, to react with the designated percentage of the benzylic hydrogens of the polystyrene. For example, a 50% cross-linked polystyrene-divinyl benzene resin contains divinyl benzene in amount sufficient to react with 50% of the polystyrene benzylic hydrogens.

These resins are macroreticular and possess physical porosity. The active sites (e.g. $SO_3H$) are accessible without the necessity of substantial swelling as contrasted with gel-type resins such as the Dowex 50WX4 used in Canadian 839,312. These latter resins have high gel phase porosity and undergo substantial swelling upon hydration.

In practice of the invention sufficient of the highly acidic resin catalyst is employed to ensure a satisfactory conversion and selectivity. It is generally advantageous to contact the reactants with a bed of the solid resin catalyst, although other techniques such as slurry contact can be used. Continuous procedures are preferred, although batch techniques can be used.

In an especially preferred embodiment of the invention, isobutane oxidate which is produced in accordance with known oxidation procedures and which is comprised mainly of TBA and TBHP, after removal of unreacted isobutane, is directly reacted to form ditertiary butyl peroxide in accordance with the invention. U.S. Pat. Nos. 2,845,461, 3,478,108 and 4,408,081 describe the isobutane oxidation.

In order to more clearly illustrate the invention, the mixture was heated to 80° C. with stirring. The results obtained are shown in the following Table I and II:

TABLE 1

| Run | Catalyst | Cat Amt[1] | Time[2] | i-C4[3] | Conv[4] | Sel[5] | H2O[6] |
|-----|----------|-----------|---------|---------|---------|--------|--------|
| 1 | XN-1010 | 10 | 4 | — | 93.1 | 86.7 | 3.029 |
| 2 | " | 10 | 3 | — | 83.3 | 87.7 | — |
| 3 | " | 5 | 4 | — | 69.0 | 74.2 | 5.479 |
| 4 | " | 10 | 4 | — | 72.1 | 75.8 | — |
| 5 | " | 10 | 4 | — | 67.5 | 78.2 | 5.249 |
| 6 | A-15 | 10 | 4 | — | 99.6 | 85.0 | — |
| 7 | " | 10 | 2 | — | 85.5 | 89.0 | 3.126 |
| 8 | " | 5 | 4 | — | 66.2 | 94.0 | — |
| 9 | " | 10 | 4 | — | 73.3 | 92.6 | 3.771 |
| 10 | XN-1010 | 10 | 4 | 3.1 | 89.2 | 94.5 | 0.598 |
| 11 | " | 10 | 4 | 1.7 | 94.7 | 85.4 | 1.308 |
| 12 | " | 10 | 2 | 3.3 | 87.2 | 80.9 | 0.426 |
| 13 | A-15 | 10 | 4 | 3.1 | 92.0 | 91.5 | 0.204 |
| 14 | " | 10 | 4 | 1.7 | 93.6 | 71.5 | 0.943 |
| 15 | " | 10 | 2 | 3.1 | 87.5 | 70.4 | 0.365 |
| 16 | Dowtex | 10 | 4 | 3.1 | 54.0 | 89.1 | 2.513 |

[1] wt % based on TBHP + TBA
[2] Reaction time, hours
[3] Mols isobutylene per mol TBHP fed
[4] Percentage of TBHP conversion based on oss of TBHP
[5] Percentage Selectivity to DTBP based on TBHP converted
[6] Percentage by weight water in product mixture Runs 1, 2, 6 and 7 were run in a Teflon lined Parr reactor;

TABLE 2

| Run | Catalyst | Cat Amt[1] | Time[2] | Prod wt[3] | Conv[4] | Sel[5] | DTBP[6] | H2O[7] |
|-----|----------|-----------|---------|-----------|---------|--------|---------|--------|
| 17 | XN-1010 | 10 | 4.5 | 72.9 | 41.0 | 86.4 | 0.153 | |
| 18 | XN-1010 | 10 | 1 | 83.5 | 24.7 | 95.9 | 0.106 | 6.664 |
| | | | 2 | 76.8 | 31.9 | 82.0 | 0.117 | 7.210 |
| | | | 3 | 72.4 | 35.9 | 90.2 | 0.145 | 7.925 |
| | | | 4 | 69.4 | 36.6 | 89.9 | 0.148 | 7.008 |
| 19 | XN-1010 | 2 | 4.5 | 74.3 | 24.9 | 51.3 | 0.059 | |
| 20 | XN-1010 | 2 | 1 | 89.9 | 12.2 | 100.0 | 0.055 | |
| | | | 2 | 85.3 | 15.2 | 117.0 | 0.080 | |
| | | | 3 | 82.9 | 20.0 | 93.5 | 0.084 | |
| | | | 4 | 77.9 | 26.4 | 75.6 | 0.090 | 8.678 |
| 21 | A-15 | 10 | 3 | 69.6 | 38.4 | 96.4 | 0.165 | 6.654 |
| 22 | A-15 | 10 | 0(8) | 88.0 | 12.9 | 96.9 | 0.055 | 3.196 |
| | | | 1 | 73.9 | 28.0 | 86.5 | 0.108 | 6.062 |
| | | | 2 | 70.6 | 30.4 | 97.1 | 0.131 | 7.494 |
| | | | 3 | 65.0 | 34.6 | 79.9 | 0.123 | 7.827 |
| | | | 4 | 62.6 | 36.6 | 97.3 | 0.156 | 7.173 |
| 23 | A-15 | 2 | 4.5 | 57.1 | 35.4 | 41.1 | 0.062 | 10.78 |
| 24 | A-15 | 2 | 1 | 82.3 | 15.9 | 107.9 | 0.076 | 6.957 |
| | | | 2 | 76.8 | 19.7 | 93.6 | 0.082 | 8.073 |
| | | | 3 | 73.5 | 21.0 | 93.2 | 0.086 | 9.768 |
| | | | 4.5 | 68.4 | 25.0 | 81.1 | 0.090 | 11.380 |

[1] wt % based on TBHP + TBA
[2] Reaction time, hours
[3] Product wt, grams
[4] Percentage of TBHP conversion based on loss of TBHP
[5] Percentage of selectivity to DTBP base on TBHP converted
[6] Mols DTBP
[7] Percentage of wt % water in product mixture
[8] Measured after heating to reacton temperature following examples are provided.

EXAMPLES

A series of reaction runs were carried out in accordance with the present invention. In each case a debutanized isobutane oxidate was reacted to form ditertiary butyl peroxide. Runs were carried out with and without added isobutylene using different resin catalysts. XN 1010 sulfonic acid resin catalyst (80% cross-linked) was employed as was Amberlyst A-15 (20% cross-linked) and Dowex 50 WX4 (4% cross-linked). The oxidate used contained about 60 wt. % TBA, 38 wt. % TBHP with the remainder comprised of methanol, acetone, water and traces of other organic materials.

In each case about 100g of the oxidate was admixed with the indicated amount of dried resin catalyst and the indicated amount of isobutylene, where used, and the In runs 17–24, the system was run under reflux. Vapors were i) removed and condensed, and condensate returned to the reactor. Isobutylene in the vapors was not condensed and returned.

From the data shown above it can be seen that the reaction of TBA and TBHP proceeds quite well to produce DTBP where highly cross-linked resin catalysts are employed, even where substantial concentrations of water are present in the reaction mixture and no isobutylene is added; see Runs 1-9. The use of the highly cross-linked resin catalysts reduces TBA dehydration and increases TBHP conversions and DTBP yields where isobutylene is added as compared to use of gel resins having low cross-linking; compare Runs 10 and 13 with Run 16 above. With gel resins, as shown in Run 16, improved TBHP conversions and DTBP yields are achieved as compared with prior art teachings where isobutylene is used in the feed.

Continuous runs were carried out in accordance with the invention using isobutane oxidate described above. The feed was continuously passed through a bed of 50 grams XN-1010 catalyst at 90° C. and 80–120 psig. The results are shown in Table III:

TABLE III

| Run | WHSV[1] | i-C4[2] | Conv.[3] | Sel.[4] | H$_2$O[5] |
|---|---|---|---|---|---|
| 25 | 2.2 | 1.3 | 90 | 95 | 2.0 |
| 26 | 4.5 | 1.3 | 80 | 94 | 2.2 |
| 27 | 0.8 | 0 | 75 | 80 | — |
| 28 | 3.4 | 0 | 50 | 85 | — |

[1]Weight of total feed per weight of catalyst per hour
[2]Mols of isobutylene per mol TBHP fed
[3]Percentage of TBHP conversion based on loss of TBHP
[4]Percentage Selectivity to DTBP based on TBHP converted
[5]Percentage by weight water in product mixture The above results in Table III demonstrate that the process of the invention can readily be practiced in the continuous mode.

I claim:

1. A process for the preparation of a dialkyl peroxide which comprises reacting a reactant selected from the group consisting of an alcohol having the formula ROH, an olefin having the formula:

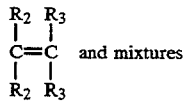

with an organic hydroperoxide having the formula R$_1$OOH in the presence of an effective amount of an acidic, at least 10% cross linked, ion exchange resin catalyst, R and R$_1$ being alkyl groups having 1 to 10 carbon atoms, and R$_2$ and R$_3$ being hydrogen or R.

2. A process for the preparation of ditertiary butyl peroxide which comprises reacting a reactant selected from the group consisting of tertiary butyl alcohol, isobutylene, and mixtures with tertiary butyl hydroperoxide in the presence of an effective amount of an acidic, at least 10% cross-linked ion exchange resin catalyst.

3. A process for the preparation of ditertiary amyl peroxide which comprises reacting a reactant selected from the group consisting of tertiary amyl alcohol, tertiary amylene, and mixtures with tertiary amyl hydroperoxide in the presence of an effective amount of an acidic, at least 10% cross-linked ion exchange resin catalyst.

4. The process of claim 1 wherein the said resin is at least 20% cross-linked polystyrene-divinyl benzene acidic resin.

5. A process for the preparation of a dialkyl peroxide which comprises reacting an olefin having the formula:

with an organic hydroperoxide having the formula R$_1$OOH in the presence of an effective amount of an acidic ion exchange resin catalyst, R$_2$ and R$_3$ being hydrogen or R, R and R$_1$ being alkyl groups having 1 to 10 carbon atoms.

6. A process for the preparation of ditertiary butyl peroxide which comprises reacting isobutylene with tertiary butyl hydroperoxide in the presence of an effective amount of an acidic ion exchange resin catalyst.

7. A process for the preparation of ditertiary amyl peroxide which comprises reacting tertiary amylene with tertiary amyl hydroperoxide in the presence of an effective amount of an acidic ion exchange resin catalyst.

* * * * *